(12) United States Patent
Hwang et al.

(10) Patent No.: US 8,420,858 B2
(45) Date of Patent: Apr. 16, 2013

(54) PROCESS FOR PREPARATION OF IOPROMIDE

(75) Inventors: Kook Sang Hwang, Daejeon (KR); Soon Min Chung, Daejeon (KR); Chang Ki Kim, Daejeon (KR); Bok Tae Kim, Daejeon (KR); Ju Young Lee, Daejeon (KR); Byeong Cheol Kim, Daejeon (KR); Goon Ho Joe, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 238 days.

(21) Appl. No.: 12/988,674

(22) PCT Filed: Apr. 17, 2009

(86) PCT No.: PCT/KR2009/001996
§ 371 (c)(1),
(2), (4) Date: Oct. 20, 2010

(87) PCT Pub. No.: WO2009/134030
PCT Pub. Date: Nov. 5, 2009

(65) Prior Publication Data
US 2011/0034730 A1      Feb. 10, 2011

(30) Foreign Application Priority Data
Apr. 30, 2008   (KR) .................. 10-2008-0040521

(51) Int. Cl.
*C07C 233/65*    (2006.01)
(52) U.S. Cl.
USPC ....................... 564/153; 424/9.452

(58) Field of Classification Search .................. 564/153; 424/9.452
See application file for complete search history.

(56) References Cited

U.S. PATENT DOCUMENTS
5,824,821 A    10/1998  Lane et al.

FOREIGN PATENT DOCUMENTS
DE    2909439    *  9/1980
KR    2000-0061780 A    10/2000
WO    WO 98/24757 A1    6/1998

OTHER PUBLICATIONS
International Search Report dated Jul. 29, 2009 for PCT/KR2009/001996.

* cited by examiner

*Primary Examiner* — Shailendra Kumar
(74) *Attorney, Agent, or Firm* — Birch, Stewart, Kolasch & Birch, LLP

(57) ABSTRACT

The present invention relates to a novel process for preparing iopromide which is used as a contrast agent for X-ray, wherein 5-methoxyacetylamino-2,4,6-triiodoisophthalic acid (2,3-diacetoxypropyl)amide chloride of formula (19) and 5-methoxyacetylamino-2,4,6-triiodoisophthalic acid [(2,3-dihydroxy-N-methylpropyl)-(2,3-diacetoxypropyl)]diamide of formula (20) are introduced as intermediates, by which a bismer by-product generated during the preparation process can be removed even without an additional removal procedure and thus iopromide with high purity can be prepared in high yield.

11 Claims, No Drawings

PROCESS FOR PREPARATION OF IOPROMIDE

This application is a 371 of PCT/KR2009/001996, filed Apr. 17, 2009.

TECHNICAL FIELD

The present invention relates to a process for preparation of iopromide, more specifically, a process for preparation of iopromide by using 5-methoxyacetylamino-2,4,6-triiodo-isophthalic acid (2,3-diacetoxypropyl)amide chloride of formula (19) and 5-methoxyacetylamino-2,4,6-triiodoisophthalic acid [(2,3-dihydroxy-N-methylpropyl)-(2,3-diacetoxypropyl)]diamide of formula (20) as intermediates.

[Formula 19]

[Formula 20]

According to the present invention, a bismer by-product generated, which causes the decrease of the purity of iopromide, during the process for preparation of iopromide can be easily removed by the simple crystallization of the intermediate of formula (19) without an additional purification procedure for the removal of the bismer by-product and eventually, the highly pure iopromide can be obtained in high yield.

BACKGROUND ART

In examinations of internal organ wherein the difference in X-ray absorption between the organ and adjacent tissues thereof is small, 'contrast agents' having different absorption rates are used to increase the difference in X-ray absorption. There are two types of the contrast agents, i.e., positive contrast agents that absorb X-ray well and negative contrast agents that transmit X-ray well, and a proper type is used according to the examination purpose.

Iopromide of the following formula (1) has been widely used as a contrast agent for X-ray. The processes for preparing iopromide are disclosed in U.S. Pat. No. 4,364,921 (Schering Corporation, Germany) and Korean Patent No. 10-0286639.

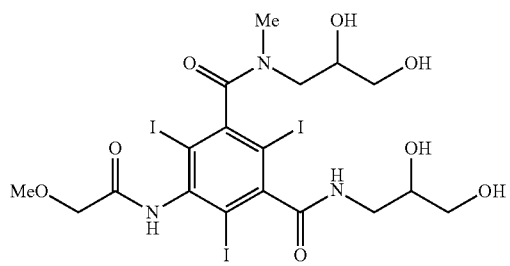

[Formula 1]

U.S. Pat. No. 4,364,921 discloses three preparation processes of iopromide. One of them is shown in the following reaction scheme 1.

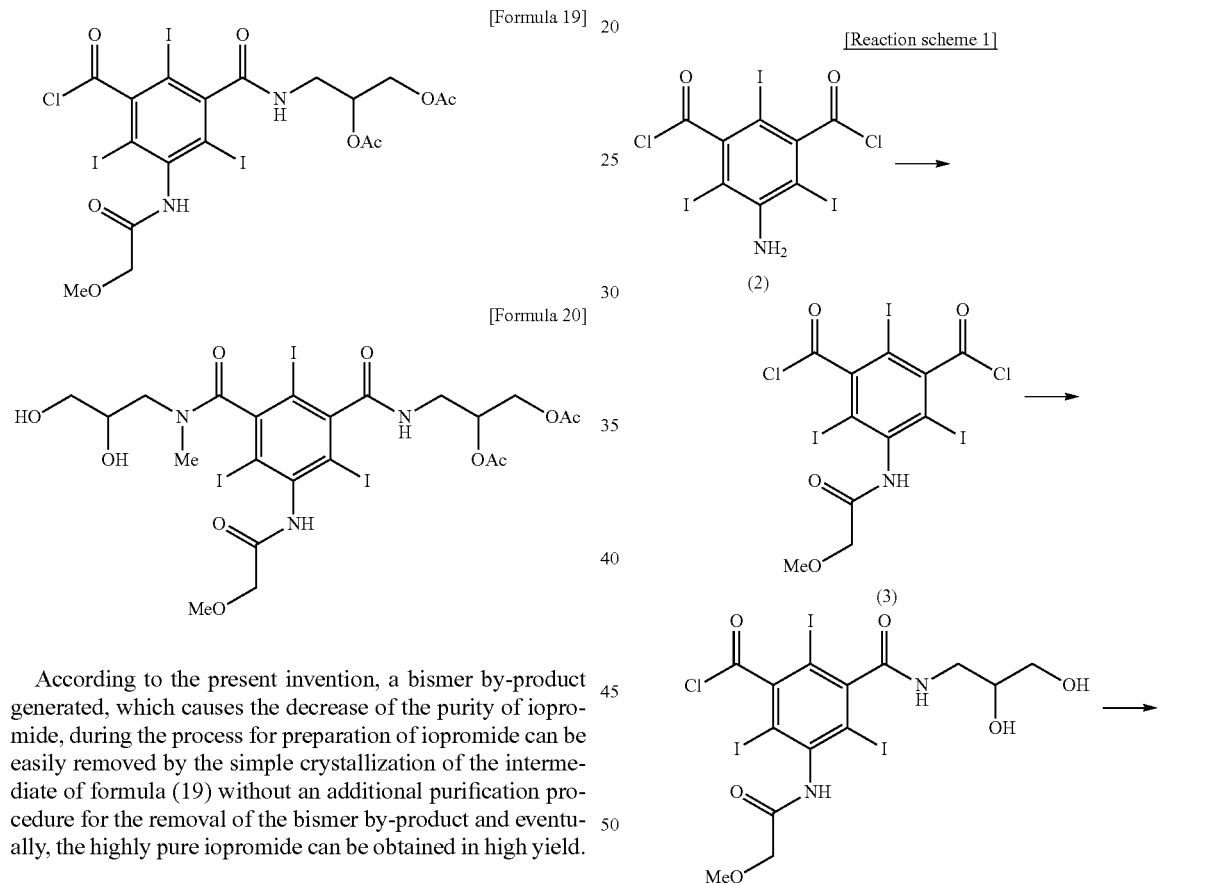

[Reaction scheme 1]

According to the above reaction scheme 1, iopromide of formula (1) is prepared through the steps of reacting 5-amino-2,4,6-triiodoisophthalic acid dichloride of formula (2) with methoxyacetyl chloride in dimethylformamide solvent to produce 5-methoxyacetylamino-2,4,6-triiodoisophthalic acid dichloride of formula (3), and reacting the compound of formula (3) with 2,3-dihydroxypropylamine and in turn with 2,3-dihydroxy-N-methylpropylamine in dimethylformamide solvent in the presence of basic material.

However, in the preparation step of 5-methoxyacetylamino-2,4,6-triiodoisophthalic acid (2,3-dihydroxypropyl) amide chloride of formula (4) by the reaction of the compound of formula (3) with 2,3-dihydroxypropylamine according to the above reaction scheme 1, a second 2,3-dihydroxypropylamine is further added to the compound of formula (4) to form a bismer by-product, 5-methoxyacetylamino-2,4,6-triiodoisophthalic acid-N,N'-bis(2,3-dihydroxypropyl)diamide of formula (5) in a large amount through the pathway of the following reaction scheme 2.

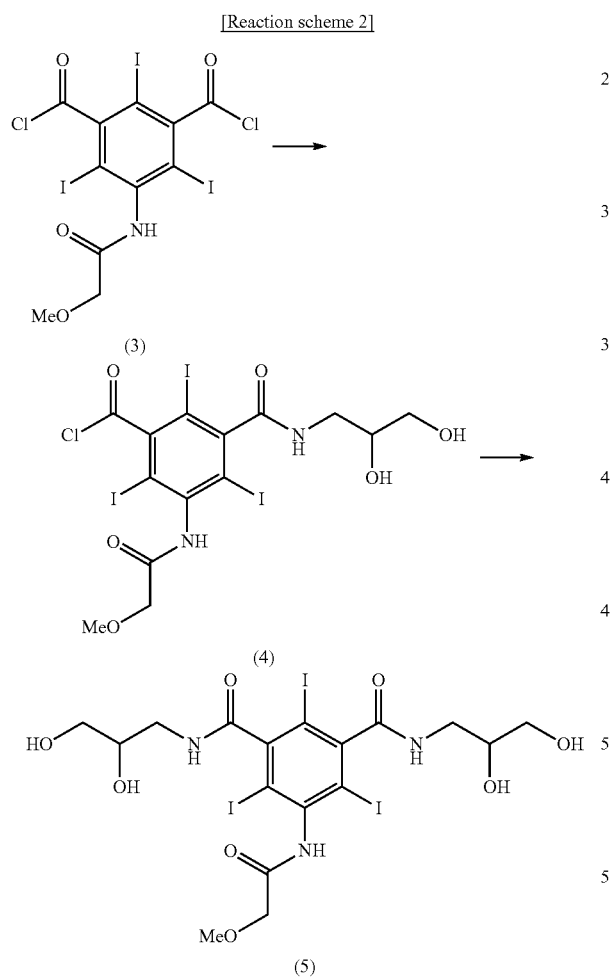

Accordingly, the inevitably produced bismer by-product of formula (5) should be removed in order to obtain iopromide with high purity. In the process according to the reaction scheme 1, the bismer by-product can be removed through a number of steps of crystallization and filtration with using large amounts of several organic solvents. However, the process according to the reaction scheme 1 must employ a number of purification steps, becomes more complicated and finally, has a demerit of decrease in productivity and in yield.

The other two processes disclosed in U.S. Pat. No. 4,364,921 are those basically under the same concept as shown in the following reaction schemes 3 and 4.

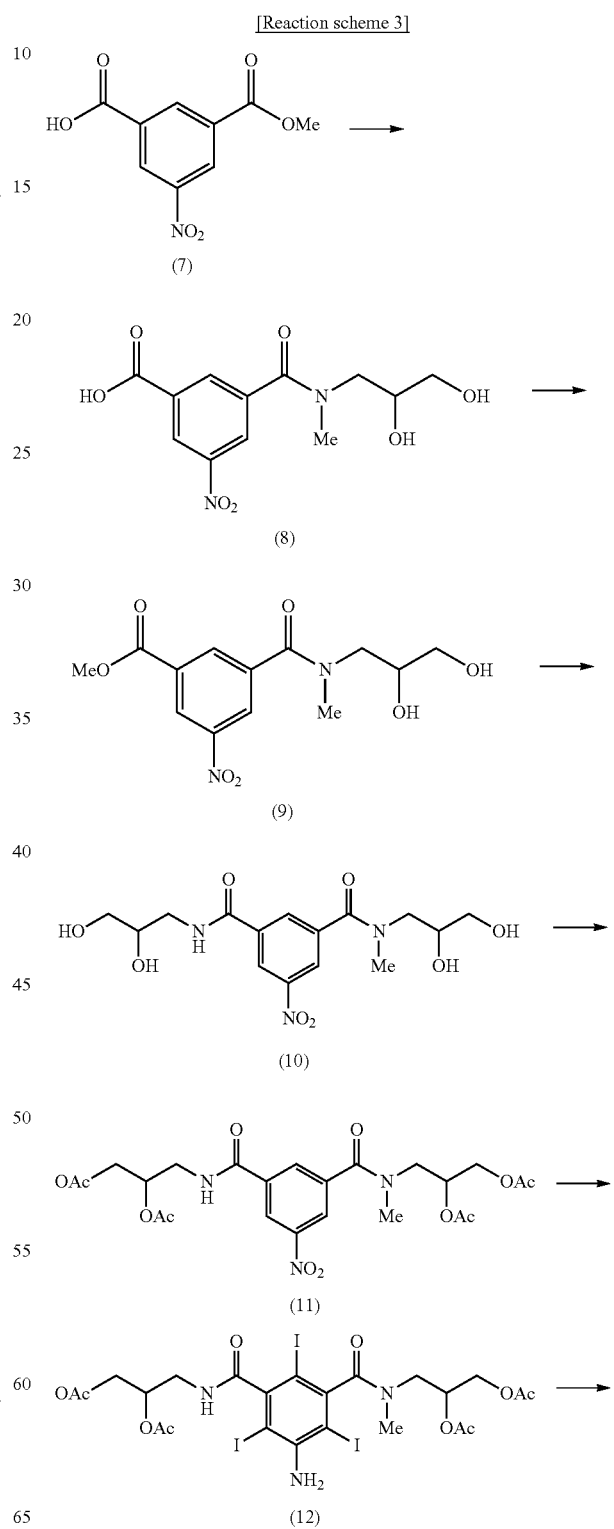

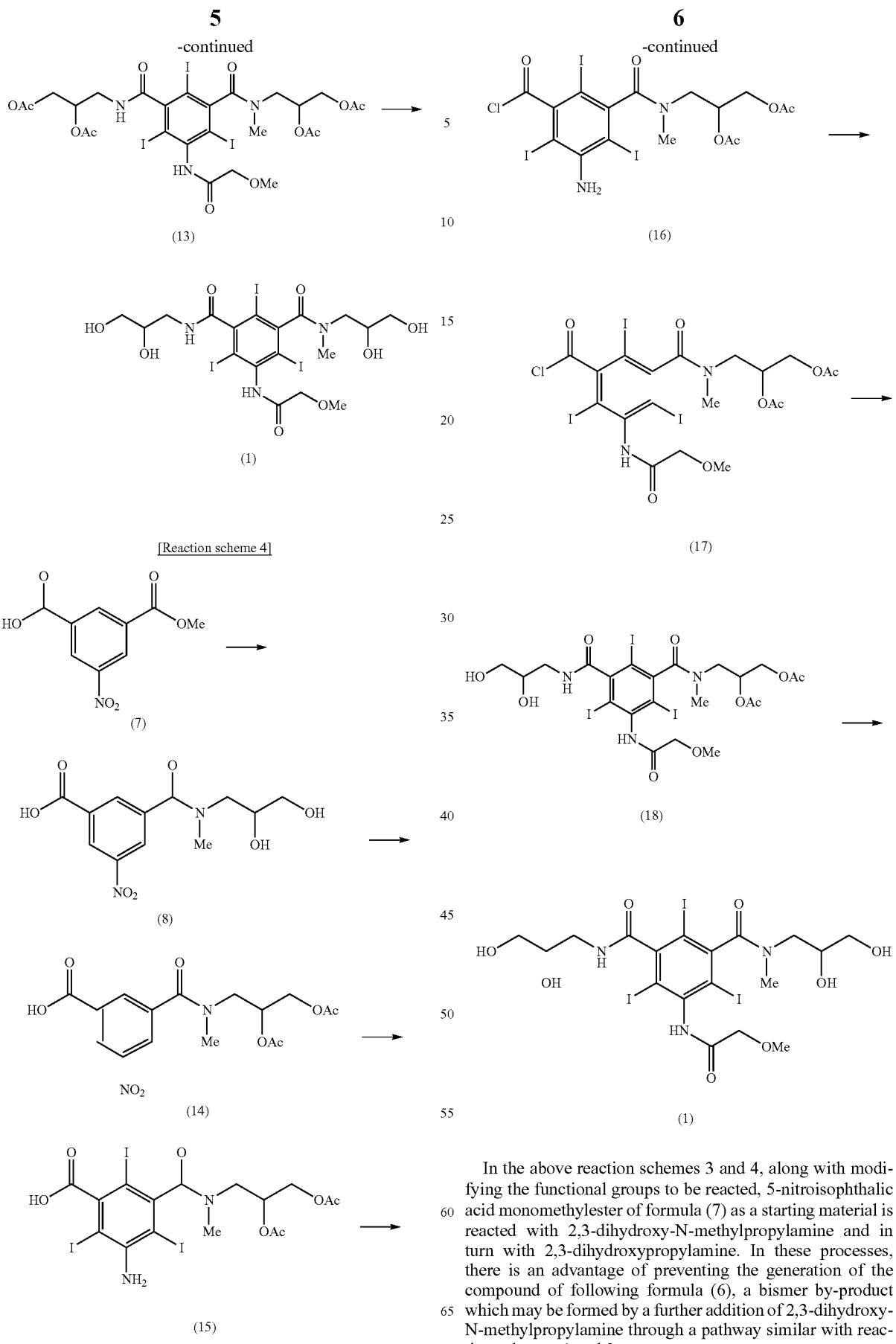

In the above reaction schemes 3 and 4, along with modifying the functional groups to be reacted, 5-nitroisophthalic acid monomethylester of formula (7) as a starting material is reacted with 2,3-dihydroxy-N-methylpropylamine and in turn with 2,3-dihydroxypropylamine. In these processes, there is an advantage of preventing the generation of the compound of following formula (6), a bismer by-product which may be formed by a further addition of 2,3-dihydroxy-N-methylpropylamine through a pathway similar with reaction schemes 1 and 2.

[Formula 6]

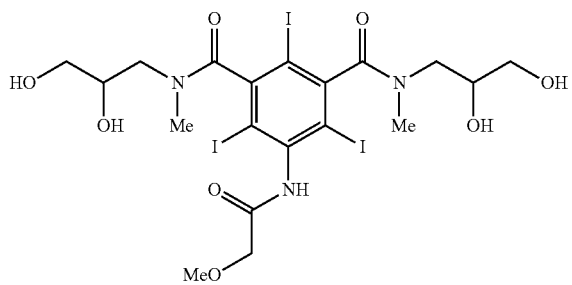

However, these processes require many steps to modify the functional groups to be reacted and also require a number of filtration and drying steps to purify the intermediates in almost every step. Therefore, similarly to the preparation process of reaction scheme 1, they are not able to avoid the low productivity and the low yield, and have a severe demerit of difficulty in industrial application.

Because of those problems being involved in the conventional processes as mentioned above, there is a considerable need to an economical process for preparing the highly pure iopromide in high yield by the effective removal of a bismer by-product.

DETAILED DESCRIPTION OF THE INVENTION

Technical Object

The purpose of the present invention is to provide an economical process for preparing the highly pure iopromide in high yield by introducing new intermediates in order to solve the foregoing problems in the conventional processes such as the bismer by-product generation in large amount, the loss of the yield and the low productivity accompanying with the removal of the bismer by-product.

Another object of the present invention is to provide new compound used as intermediate during the process for preparing iopromide.

Technical Means

The present invention relates to a process for preparing iopromide of formula (1) by using 5-methoxyacetylamino-2,4,6-triiodoisophthalic acid (2,3-diacetoxypropyl)amide chloride of formula (19) and 5-methoxyacetylamino-2,4,6-triiodoisophthalic acid [(2,3-dihydroxy-N-methylpropyl)-(2,3-diacetoxypropyl)]diamide of formula (20) as intermediates.

[Formula 19]

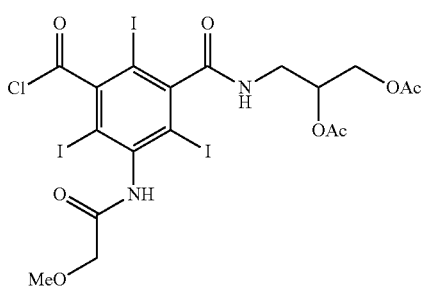

[Formula 20]

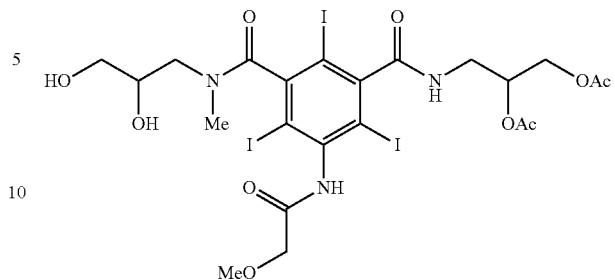

[Formula 1]

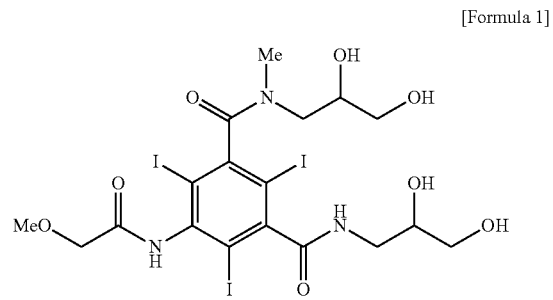 [SMILES: COCC(=O)Nc1c(I)c(C(=O)NCC(O)CO)c(I)c(C(=O)N(C)CC(O)CO)c1I]

The present invention also relates to 5-methoxyacetylamino-2,4,6-triiodoisophthalic acid [(2,3-dihydroxy-N-methylpropyl)-(2,3-diacetoxypropyl)]diamide of formula (20) that are used as intermediate during the process for preparing iopromide.

Effect

According to the present invention, since 5-methoxyacetylamino-2,4,6-triiodoisophthalic acid (2,3-diacetoxypropyl)amide chloride of formula (19) and 5-methoxyacetylamino-2,4,6-triiodoisophthalic acid [(2,3-dihydroxy-N-methylpropyl)-(2,3-diacetoxypropyl)]diamide of formula (20) are introduced as intermediates in iopromide preparation process and a bismer by-product generated can be effectively removed by the simple crystallization of intermediate of formula (19), the iopromide with high purity can be prepared in high yield without additional purification steps for the removal of the bismer by-product.

Embodiments for Carrying Out the Invention

The present invention relates to a process for preparing iopromide of formula (1) by using 5-methoxyacetylamino-2,4,6-triiodoisophthalic acid(2,3-diacetoxypropyl)amide chloride of formula (19) and 5-methoxyacetylamino-2,4,6-triiodoisophthalic acid [(2,3-dihydroxy-N-methylpropyl)-(2,3-diacetoxypropyl)]diamide of formula (20) as intermediates.

The process for preparing iopromide of formula (1) according to the present invention is shown in the following reaction scheme 5.

[Reaction scheme 5]

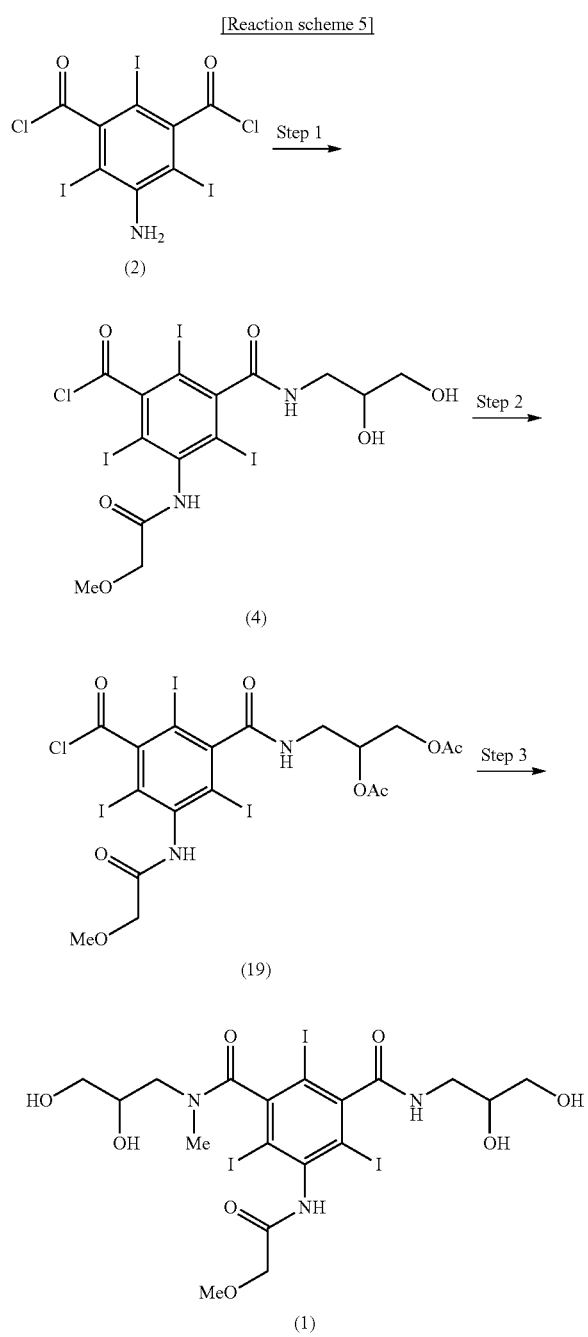

[Reaction scheme 6]

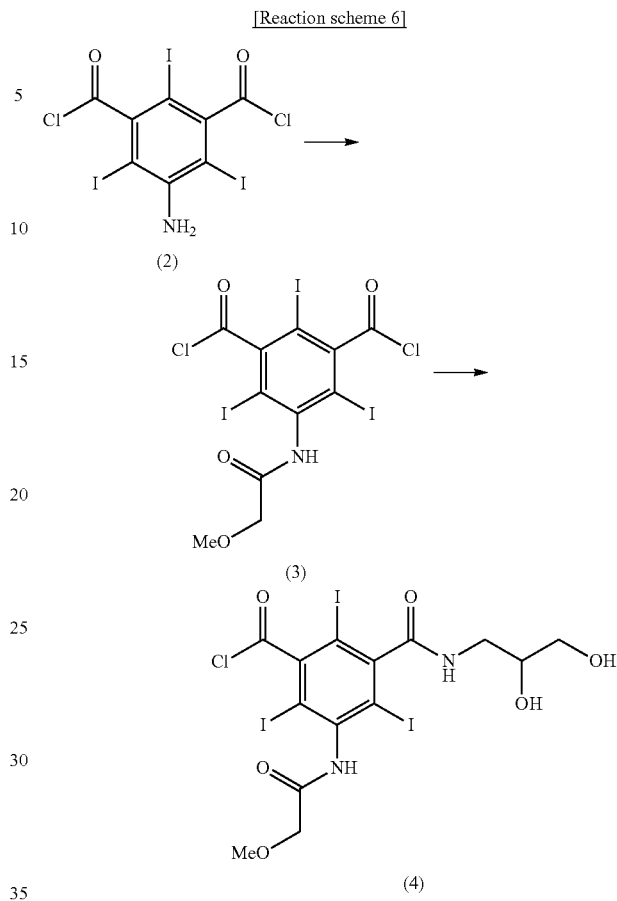

In the above reaction scheme, if 2,3-dihydroxypropylamine is used preferably in 0.6 to 1 equivalents, more preferably in 0.7 equivalents, the compound of formula (4) can be obtained in reasonable yield with minimizing the generation of the compound of formula (5) which is a bismer by-product.

In addition, since the unreacted compound of formula (3) existing in the filtrate obtained along with the compound of formula (4) can be recycled to the next batch without an additional recovery procedure, the loss of the yield of iopromide which occurs during the removal procedure of the bismer by-product generated in a large amount in conventional process can be prevented ultimately.

Step 2

The compound of formula (4) is reacted with acetic anhydride in acetic acid solvent in the presence of sulfuric acid as a catalyst to convert into the compound of formula (19). Sulfuric acid of preferably 0.01 to 0.2 moles, more preferably 0.05 to 0.1 moles per 1 molar reaction is added at a temperature of preferably from 0 to 30° C., more preferably from 5 to 25° C. Acetic anhydride of preferably 0.19 to 1 L, more preferably 0.35 to 0.7 L per 1 molar reaction is used.

5-methoxyacetylamino-2,4,6-triiodoisophthalic acid-N,N'-bis-(2,3-diacetoxypropyl) diamide of the compound of following formula (21), which is generated by a simultaneous conversion of the bismer by-product of formula (5) already produced in the step 1 with the conversion of the compound of formula (4) into the compound of formula (19), is easily removed by the simple crystallization procedure of the compound of formula (19). That is, the by-product of the compound of formula (21) can be removed even without an addi- Step 1

5-amino-2,4,6-triiodoisophthalic acid dichloride of formula (2) is used as a starting material. The compound of formula (2) is reacted with methoxyacetyl chloride in dimethylacetamide solvent to produce 5-methoxyacetylamino-2,4,6-triiodoisophthalic acid dichloride of formula (3) which is then used without an additional purification procedure for the next step. The compound of formula (3) is reacted with 2,3-dihydroxypropylamine in dimethylacetamide solvent in the presence of triethylamine to form 5-methoxyacetylamino-2,4,6-triiodoisophthalic acid (2,3-dihydroxypropyl)amide chloride of formula (4), as shown in the following reaction scheme 6.

tional removal procedure. It consequently means that the bismer by-product of the compound of formula (5) which is hard to remove according to conventional process can be effectively removed in the present invention even without any additional purification procedures.

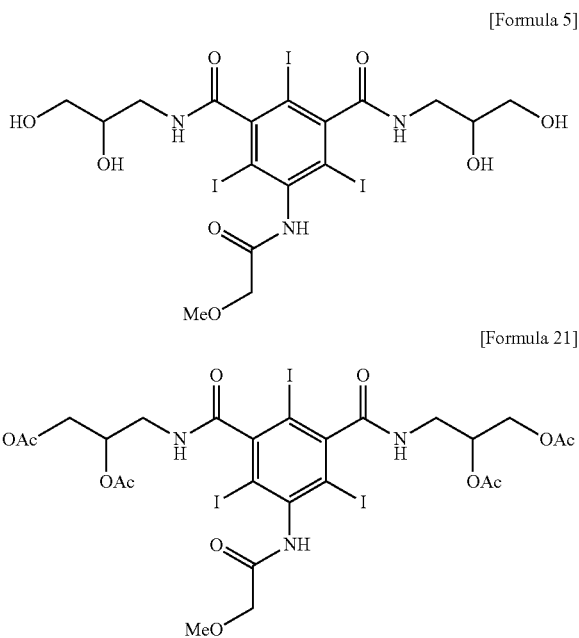

[Formula 5]

[Formula 21]

Step 3

The compound of formula (19) is reacted with 2,3-dihydroxy-N-methylpropylamine in dimethylacetamide solvent in the presence of triethylamine as a base to convert into the compound of formula (20). By the hydrolysis of the compound of formula (20) in aqueous NaOH solution without further purification therefor, iopromide of formula (1) can be obtained.

The present invention will be explained more specifically by the following examples. However, the examples are not intended to limit the scope of the present invention thereto.

Example 1

Synthesis of 5-methoxyacetylamino-2,4,6-triiodoisophthalic acid (2,3-dihydroxypropyl)amide chloride (Formula 4)

5-amino-2,4,6-triiodoisophthalic acid dichloride (13.7 kg, 23 mol) was dissolved in dimethylacetamide (17.2 kg) and the mixture was cooled to 15° C. Methoxyacetyl chloride (3.74 kg, 34.5 mol) was added dropwise thereto for 2 hours, and then the mixture was stirred for 15 hours. After confirming the disappearance of the starting material by HPLC analysis for reaction, methylene chloride (45.7 kg) and water (11.5 kg) were subsequently added to the reaction mixture upon being stirred, and then the stirring was stopped and the layers became separated. The obtained organic layer was washed with aqueous sodium bicarbonate solution and concentrated by distillation under reduced pressure. To a solution of the obtained concentrate dissolved in dimethylacetamide (43.1 kg), triethylamine (1.95 kg, 19.32 mol) was added and then a solution of 2,3-dihydroxypropylamine (1.47 kg, 16.13 mol) dissolved in dimethylacetamide (10.78 kg) was added dropwise thereto for 5 hours with maintaining 0 to 5° C. After additional 3 hours with stirring, the reaction mixture was concentrated by distillation under reduced pressure and to the concentrate, methylene dichloride (213.33 kg) was added dropwise for 5 hours to form solid. The solid was filtered and the title compound was obtained as a white solid (10.98 kg, yield 66.1%).

$^1$H NMR (dmso-d$^6$, 500 MHz) 10.2, 10.06 (2s, 1H); 8.79, 8.71, 8.63 (3t, 1H); 4.5~4.0 (br, 2H); 4.04, 4.00 (2s, 2H); 3.71~3.66 (m, 1H); 3.48, 3.47 (2s, 3H); 3.40~3.36 (m, 2H); 3.36~3.27 (m, 1H); 3.2~3.09 (m, 1H)

Example 2

Synthesis of 5-methoxyacetylamino-2,4,6-triiodoisophthalic acid (2,3-diacetoxypropyl)amide chloride (Formula 19)

5-methoxyacetylamino-2,4,6-triiodoisophthalic acid (2,3-dihydroxypropyl)amide chloride (9.97 kg, 13.8 mol) was dispersed in acetic acid, and then anhydrous acetic acid (7.45 kg) was added thereto and the mixture was cooled to 5° C. Sulfuric acid (135 g) was slowly added thereto and the mixture was stirred for 1 hour. To the obtained clear solution, sodium acetate trihydrate (376 g) was added and dissolved at 0 to 5° C. And then water (96.6 kg) was added for 3 hours with maintaining 0 to 10° C. to produce solid. The produced solid was filtered and the title compound was obtained as a white solid (10.04 kg, yield 90.2%).

$^1$H NMR (dmso-d$^6$, 500 MHz) 10.12, 9.99 (2s, 1H); 8.91, 8.80 (2t, 1H); 5.10~5.06 (m, 1H); 4.32~4.27 (m, 1H); 4.20~4.16 (m, 1H); 4.01, 4.00 (2s, 2H); 3.52~3.37 (m, 2H); 3.47, 3.46 (2s, 3H); 2.02 (s, 6H)

Example 3

Synthesis of 5-methoxyacetylamino-2,4,6-triiodoisophthalic acid [(2,3-dihydroxy-N-methylpropyl)-(2,3-dihydroxypropyl)]diamide (iopromide)

5-methoxyacetylamino-2,4,6-triiodoisophthalic acid (2,3-diacetoxypropyl)amide chloride (7.23 kg, 8.97 mol) was dissolved in dimethylacetamide (12.6 kg), and triethylamine (1.95 kg, 19.32 mol) was added thereto and a solution of 2,3-dihydroxy-N-methylpropylamine (943 g, 8.97 mol) dissolved in dimethylacetamide (4.2 kg) was added dropwise thereto at room temperature. After additional 2 hours with stirring, the solution was concentrated by distillation under reduced pressure. To an aqueous solution of the obtained 5-methoxyacetylamino-2,4,6-triiodoisophthalic acid [(2,3-dihydroxy-N-methylpropyl)-(2,3-diacetoxypropyl)]diamide dissolved in water, a solution of sodium hydroxide (897 g, 22.43 mol) dissolved in water was added and the reaction mixture was stirred for 10 hours with maintaining 20 to 25° C. The reaction solution was passed through cation exchange resin column and anion exchange resin column to produce a colorless and transparent aqueous solution. The obtained aqueous solution was distilled under reduced pressure to remove water completely, crystallized in ethanol and filtered to obtain a white crystalline iopromide (6.032 kg, yield 85%).

$^1$H NMR (dmso-d$^6$, 500 MHz) 10.07, 10.03, 9.97, 9.90 (4s, 1H); 8.66, 8.57, 8.52 (3t, 1H); 4.76~4.74 (m, 1H); 4.72, 4.67 (2t, 1H); 4.59~4.58 (m, 1H); 4.54~4.44 (m, 1H); 4.00 (s, 2H); 3.89~3.88 (m, 1H); 3.69~3.68 (m, 2H); 3.47 (s, 3H); 3.44~3.38 (m, 4H); 3.23~3.17 (m, 3H), 2.85~2.83 (4s, 3H)

Example 4

Synthesis of 5-methoxyacetylamino-2,4,6-triiodo-isophthalic acid [(2,3-dihydroxy-N-methylpropyl)-(2,3-diacetoxypropyl)]diamide (Formula 20)

5-methoxyacetylamino-2,4,6-triiodoisophthalic acid (2,3-diacetoxypropyl)amide chloride (80.65 g, 0.1 mol) was dissolved in dimethylacetamide (140.5 g), and then triethylamine (11.13 g, 0.11 mol) was added thereto and a solution of 2,3-dihydroxy-N-methylpropylamine (10.5 g, 0.1 mol) dissolved in dimethylacetamide (46.9 g) was added dropwise thereto at room temperature. After additional 2 hours with stirring, the produced solid was filtered and then the filtrate was concentrated by distillation under reduced pressure. To the obtained concentrate, diethyl ether was added dropwise to form solid. The formed solid was filtered and the title compound was obtained as a white solid (85.8 g, yield 98%).

$^1$H NMR (dmso-d$^6$, 500 MHz) 10.10, 10.06, 10.00, 9.92 (4s, 1H); 8.93, 8.83, 8.78 (3m, 1H); 5.09 (br, 1H); 4.78~4.74 (m, 1H); 4.62~4.58 (m, 1H); 4.34~4.26 (m, 1H); 4.22~4.16 (m, 1H); 4.00 (s, 2H); 3.89 (br, 1H); 3.72~3.65, (m, 1H); 3.49~3.40 (br, 2H); 3.47 (s, 3H); 3.48~3.38 (m, 2H); 3.22~3.12, (m, 1H); 3.07~3.04 (m, 1H); 2.87~2.82 (m, 2H); 2.03 (s, 3H); 2.02 (s, 3H)

The invention claimed is:

1. A process for preparing iopromide of formula (1), wherein iopromide of formula (1) is prepared according to reaction scheme 5:

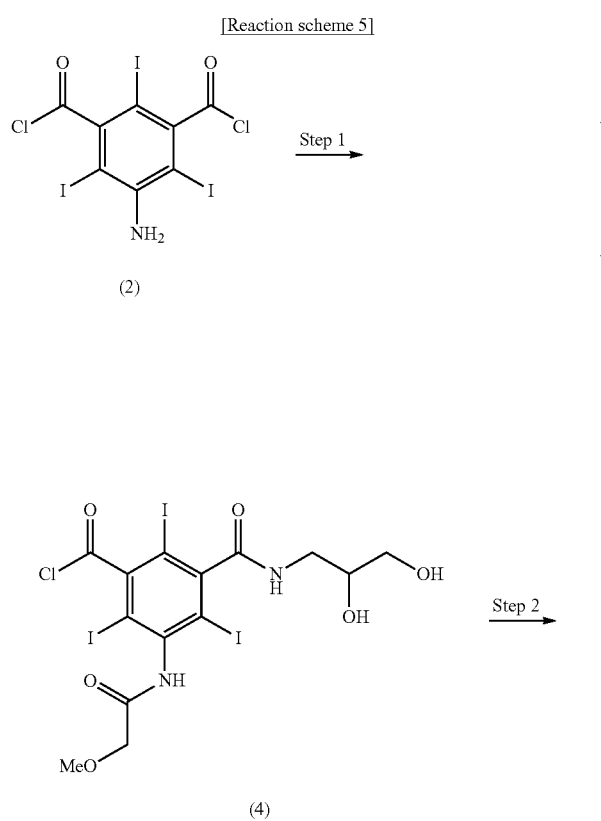

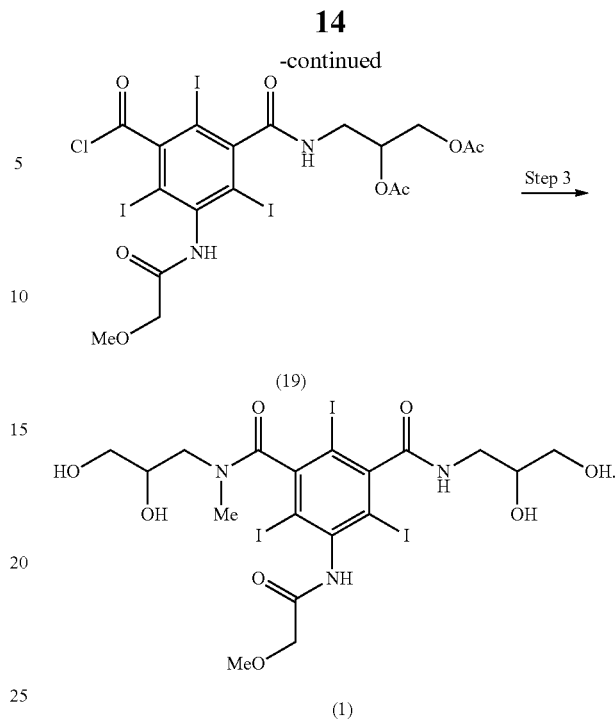

2. The process according to claim 1, wherein the compound of formula (4) is synthesized according to reaction scheme 6:

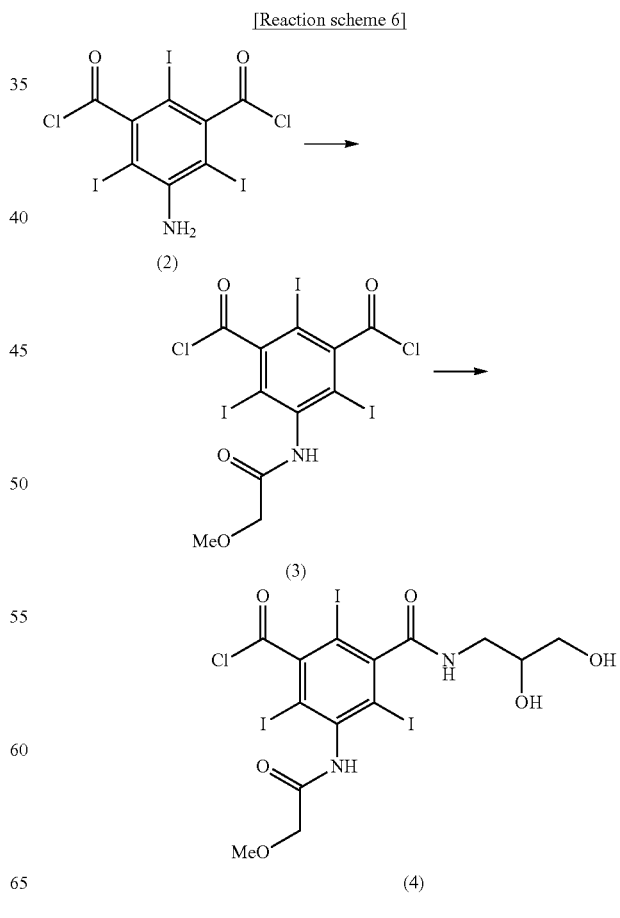

wherein the compound of formula (2) is reacted with methoxyacetyl chloride in dimethylacetamide solvent to synthesize the compound of formula (3) and the compound of formula (3) is reacted with 2,3-dihydroxypropylamine in dimethylacetamide solvent in the presence of triethylamine to synthesize the compound of formula (4).

3. The process according to claim 2, wherein the compound of formula (3) is reacted with 0.6 to 1.0 equivalents of 2,3-dihydroxypropyl amine.

4. The process according to claim 3, wherein the compound of formula (3) is reacted with 0.7 equivalents of 2,3-dihydroxypropyl amine.

5. The process according to claim 2, wherein the compound of formula (3) existing in the filtrate generated during a purification procedure of the compound of formula (4) is recycled.

6. The process according to claim 1, wherein the compound of formula (4) is reacted with acetic anhydride in acetic acid solvent in the presence of sulfuric acid catalyst and converted to the compound of formula (19).

7. The process according to claim 6, wherein the sulfuric add of 0.01 to 0.2 mole per 1 molar reaction is added at the temperature of 0 to 30° C. and acetic anhydride of 0.19 to 1.0 L per 1 molar reaction is used.

8. The process according to claim 1, wherein 5 methoxyacetylamino-2,4,6-triiodoisophthalic acid-NnN'-bis(2,3-dihydroxypropyl)diamide of formula (5) obtained in the step 1 is converted into 5-methoxyacetylamino-2,4,6-triiodoisophthalic acid-N,N-bis(2,3-diacetoxypropyl)diamide of formula (21):

9. The process according to claim 8, wherein the compound of formula (21) is removed through a purification procedure of the compound of formula (19).

10. The process according to claim 1, wherein the compound of formula (19) is reacted with 2,3-dihydroxy-N-methylpropylamine in dimethylacetamide solvent in the presence of triethylamine to synthesize the compound of formula (20) and the compound of formula (20) is hydrolyzed in aqueous NaOH solution:

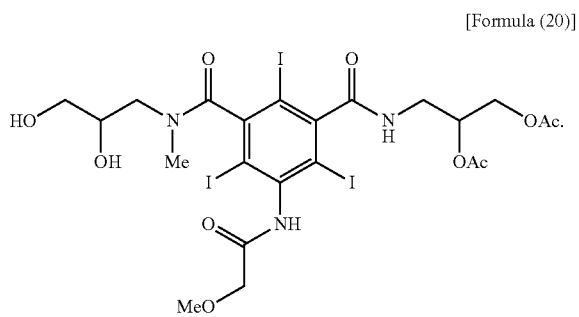 [SMILES: COCC(=O)Nc1c(I)c(C(=O)NCC(COC(C)=O)OC(C)=O)c(I)c(C(=O)N(C)CC(O)CO)c1I]

[Formula (20)]

11. A compound of formula (20):

[Formula (5)]

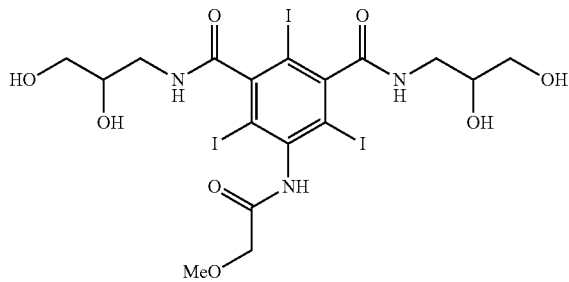

[Formula (21)]

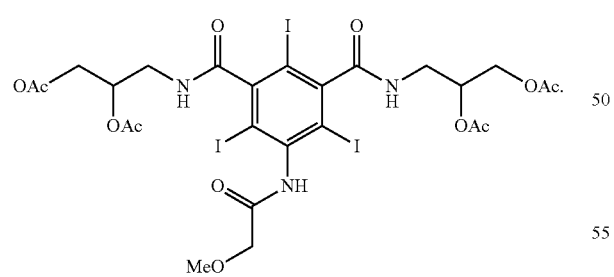

[Formula (20)]

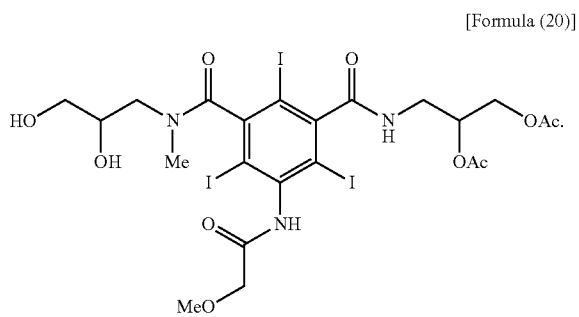 [SMILES: COCC(=O)Nc1c(I)c(C(=O)NCC(COC(C)=O)OC(C)=O)c(I)c(C(=O)N(C)CC(O)CO)c1I]

* * * * *